United States Patent
Frater et al.

(12)

(10) Patent No.: US 6,844,470 B2
(45) Date of Patent: Jan. 18, 2005

(54) PROCESS FOR THE PURIFICATION OF 1,3-DIKETONES

(75) Inventors: Georg Frater, Winterthur (CH); Ulrich Huber, Erlenbach (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 10/470,893

(22) PCT Filed: Jan. 24, 2002

(86) PCT No.: PCT/EP02/00697

§ 371 (c)(1),
(2), (4) Date: Aug. 1, 2003

(87) PCT Pub. No.: WO02/062738

PCT Pub. Date: Aug. 15, 2002

(65) Prior Publication Data

US 2004/0068145 A1 Apr. 8, 2004

(30) Foreign Application Priority Data

Feb. 2, 2001 (EP) .......................................... 01102396

(51) Int. Cl.$^7$ ...................... C07C 45/00; C07C 49/163
(52) U.S. Cl. ...................... 568/324; 568/325; 568/331; 568/338; 568/366
(58) Field of Search ................................ 568/324, 338, 568/366, 325, 331

(56) References Cited

U.S. PATENT DOCUMENTS

| 2,401,335 A | 6/1946 | Calder et al. ............... 260/593 |
| 3,742,062 A | 6/1973 | Chappelow, Jr. et al. ... 260/592 |
| 3,919,275 A | 11/1975 | Rothman et al. ........ 260/438.1 |

FOREIGN PATENT DOCUMENTS

| GB | 868106 | 5/1961 |
| GB | 869988 | 6/1961 |

OTHER PUBLICATIONS

Chow, Y.L., et al., "Spectroscopic and Electrochemical Properties of 1,3–Diketonatoboron Derivatives," *Journal of Physical Organic Chemistry*, vol. 9, pp. 7–16 (1996).

Primary Examiner—Samuel Barts
Assistant Examiner—Sikarl A. Witherspoon
(74) Attorney, Agent, or Firm—Bryan Cave LLP

(57) ABSTRACT

A process for the purification of 1,3-diketones comprising reacting a 1,3-diketone with an earth metal or alkaline earth metal complexing agent in an organic solvent, isolating, washing and decomposing the resulting complex, and isolating the purified 1,3-diketone.

20 Claims, No Drawings

PROCESS FOR THE PURIFICATION OF 1,3-DIKETONES

The present invention relates to a novel process for the purification of 1,3-diketones or for isolating pure 1,3-diketones from reaction mixtures containing such 1,3-diketones.

The process in accordance with the present invention comprises
- a) reacting a 1,3-diketone with an earth metal or alkaline earth metal complexing agent in an organic solvent to form a complex,
- b) isolating said complex,
- c) washing said complex with an organic solvent,
- d) decomposing said complex, and
- e) isolating the purified 1,3-diketone.

In a preferred aspect, the invention is concerned with the purification or isolation of 1,3-diketones of the formula $R^1$—CO—$CH_2$—CO—$R^2$ wherein $R^1$ and $R^2$ are independently an aliphatic, aromatic or heterocyclic moiety. Examples of aliphatic moieties represented by $R^1$ and/or $R^2$ are saturated aliphatic moieties, e.g. $C_{1-20}$-alkyl groups, and unsaturated aliphatic moieties, e.g. $C_{2-20}$-alkenyl or alkinyl groups, which may be straight chain or branched and may be unsubstituted or substituted, e.g., by halogen, hydroxy, lower alkoxy or lower alkanoyloxy.

Examples of aromatic moieties $R^1$ and $R^2$ are mono and bicyclic moieties such as phenyl and naphthyl which may be unsubstituted or substituted. Examples of heterocyclic moieties are mono- and bicyclic heterocycles containing one or more nitrogen, sulfur and/or oxygen atoms as the hetero atoms, such as pyridyl, pyrimidyl, thienyl, furyl, thiazolyl, indolyl, quinolinyl and isoquinolinyl.

In a particularly preferred aspect, the 1,3-diketone is 4-tert.butyl-4'methoxy-dibenzoylmethane or isopropyl dibenzoylmethane, also known as PARSOL® 1789 and EUSOLEX® 8020, respectively, which are a widely used UV filter in cosmetic sunscreen formulations. 4-tert.butyl-4'methoxy-dibenzoylmethane is conventionally prepared by aldol condensation of a 4-tert.-butyl benzoic acid derivative with 4-methoxy acetophenon and is purified by recrystallisation of the crude condensation product from methanol. By the process of the present invention the diketones such as 4-tert.butyl-4'methoxy-dibenzoylmethane can be obtained in higher purity. This is particularly important because minor impurities tend to impart a color to the product which is unwanted for use in cosmetic formulations.

The organic solvent used in the purification process of the present invention can be any organic solvent that is capable of solubilizing the 1,3-diketone to be purified and which is inert towards the complexing agent. Typical solvents are aromatic hydrocarbons, such as benzene and, preferably, toluene. Examples of other solvents for use in the present invention are aliphatic alcohols such as methanol and ethanol, ethers, such as diethyl ether, methyl tert.butyl ether, tetrahydrofuran and dioxane, and chlorinated hydrocarbons such as methylene chloride, chloroform and chlorobenzene.

The earth metal or alkaline earth metal complexing agent can be any derivative of these metals which are capable to form a complex with 1,3-diketones. Typical examples are halogenides of boron, aluminum, calcium and magnesium, in particular boron trifluoride, aluminum trichloride, calcium chloride and magnesium chloride, as well as boric acid. The preferred complexing agent is boron trifluoride.

The purification process can be carried out by adding the complexing agent to a solution of crude 1,3-diketone in an appropriate organic solvent, or by adding the complexing agent to a reaction mixture containing the 1,3-diketone. Suitably, equimolar amounts of the 1,3-diketone and the complexing agent, preferably a slight excess, e.g., a 10% molar excess of the complexing agent are used. Upon reaction of the 1,3-diketone with the complexing agent a complex is formed as a solid precipitate which can be separated and washed with an appropriate solvent, suitably the same solvent as the one used for dissolving the crude product or the solvent wherein the reaction for the preparation of the 1,3-diketone was carried out. After washing, the solid precipitate can be decomposed by treatment with an aqueous medium comprising a base thus yielding the 1,3-diketone in high purity. The base can be any base which is soluble in aqueous media, such as aqueous ammonia, alkali hydroxides, carbonates or hydrogencarbonates, e.g. NaOH, KOH, $Na_2CO_3$ or $NaHCO_3$. Preferred is aqueous ammonia. Suitably, the base is used in an equimolar amount with respect to the 1,3-diketone complex or in slight molar excess, e.g. in 10% molar excess. The decomposition of the 1,3-diketone complex is suitably carried out in a solvent such as specified earlier, particularly in an alkanol such as methanol. In another embodiment of the invention the pure diketone can be obtained from the complex by treatment with an acid which is soluble in aqueous media and which is capable of forming complexes with the complexing agent, such as oxalic acid.

The invention is illustrated in more detail by the following Examples.

EXAMPLE 1 a) 36 g (1.2 mol) of 80% sodium amide and 300 g of dry toluene were added to a round bottom flask, which was flushed with nitrogen. The mixture was heated to 50° C. and 150.2 g (1 mol) of acetylanisole in 309 g of toluene were added within 1.5 hours. After completion of the addition, the mixture was held at 50° C. for 15 minutes whereupon 192.3 g (1 mol) of p-tert.butylbenzoic acid methyl ester (prepared according to U.S. Pat. No. 4,387,089) were added at this temperature within 1 hour and 50 minutes. The mixture was stirred for a further 1 hour at 50° C. and then heated at 100° C. for 1 hour, after which time the product separated out in the form of a solid precipitate. The mixture was left to stand for 12 hours. 300 ml of ice-water followed by a mixture of 100 ml of pure hydrochloric acid and 250 ml of ice-water then added. The phases were separated and the organic phase washed twice with water and dried over sodium sulfate.

b) To the organic phase obtained in step a) 140 ml (1.1 mol) of boron trifluoride diethyl etherate were added dropwise. When the addition was finished, the solution was dark brown. After 5 minutes a precipitate was formed and the mixture became red-brown. The mixture was then heated to 120° C. (reflux temperature) for 1 hour. Its color changed again, from red-brown to pink-violet. The mixture was cooled to room temperature, the precipitate was filtered and washed with 600 ml of tert.-butyl methyl ether. After drying at high vacuum, 240 g of $BF_3$-complex of 4-tert. butyl-4'-methoxy-dibenzoylmethane was obtained as a yellow-green fluorescent solid product.

c) A 6 liter three necked reaction flask equipped with reflux condenser, stirrer and oil bath was charged with 240 g (0.67 mol) of $BF_3$-complex of 4-tert. butyl-4'-methoxy-dibenzoylmethane as obtained in step b), 3.5 liter of methanol and 50 g of aqueous ammonia (25%). The mixture was heated to 70° C. (reflux temperature) overnight under stirring. A clear solution was formed. After cooling with an ice bath a precipitate was formed which was filtered off and washed with 1 liter of aqueous methanol (75%). After drying at high vacuum, 196 g of 4-tert. butyl-4'-methoxy-dibenzoylmethane of m.p. 85.5° C. were obtained. Purity by HPLC: 99.7%.

EXAMPLE 2 a) A part of the organic phase obtained in example 1, step a) was concentrated and dried at high vacuum and 5 g of a brown, semicrystalline material was obtained, which contained 70% of 4-tert. butyl-4'-methoxy-dibenzoylmethane as determined by HPLC. This material was dissolved in 15 ml of ethanol and heated to 60° C. In a separate flask, 0.72 g of $AlCl_3$ was dissolved in 15 ml of ethanol, which caused an exothermic reaction. This solution was slowly added to the first one. This combined yellow solution was treated with 2 ml of aqueous ammonia (25%) and pale yellow crystals were immediately formed. The reaction was stirred for a further 15 min at 60° C., cooled and filtered off. The residue was washed with water and ethanol and dried at the high vacuum. 4.3 g of pale orange crystals of the corresponding $Al^{+3}$-complex were obtained. MS: 954 ($M^+$); 645 (100%).

b) A 250 ml three necked reaction flask equipped with reflux condenser, stirrer and oil bath was charged with 4.1 g of the $Al^{+3}$-complex of 4-tert.butyl-4'-methoxy-dibenzoylmethane as obtained in example 2 step a) dissolved in 50 ml of methanol and 1 ml of aqueous ammonia (25%). The mixture was heated to reflux and 0.82 g of oxalic acid dihydrate was added and the hot solution was filtered. The filtrate was cooled and 4-tert.butyl-4'-methoxy-dibenzylmethane precipitated. The precipitate was filtered off and dried at high vacuum to yield 2.33 g of pure product mentioned above. The filtrate was treated with a small amount of water and a second fraction of 4-tert.butyl-4'-methoxy-dibenzoylmethane precipitated, which was filtered off and dried to yield another 1 g of pure product.

EXAMPLE 3

In analogy to the procedure described in example 2a) but using $MgCl_2$ instead of $AlCl_3$ the $MgCl_2$ complex of 4-tert.-butyl-4'-methoxy dibenzoylmethane was obtained from which pure, white 4-tert.butyl-4'-methoxy dibenzoylmethane was obtained in analogy to Example 2b).

EXAMPLE 4

In analogy to the procedure described in example 2a) but using $CaCl_2$ instead of $AlCl_3$, the $CaCl_2$ complex of 4-tert.-butyl-4'-methoxy dibenzoylmethane was obtained from which pure, white 4-tert.butyl-4'-methoxy dibenzoyl-methane was obtained in analogy to Example 2b).

What is claimed is:

1. A process for the purification of 1,3-diketones which comprises
   a) reacting a 1,3-diketone with a boron, aluminum, calcium or magnesium complexing agent in an organic solvent to form a complex,
   b) isolating said complex,
   c) washing said complex with an organic solvent,
   d) decomposing said complex, and
   e) isolating the purified 1,3-diketone.

2. A process according to claim 1 wherein the complexing agent is boron trifluoride.

3. The process according to claim 1 wherein the organic solvent used in the reaction is an aromatic hydrocarbon.

4. The process according to claim 3, wherein the aromatic hydrocarbon is toluene.

5. The process according to claim 1 wherein the complex is decomposed by treatment with aqueous ammonia solution.

6. The process according to any one of claim 1 wherein the 1,3-diketone is a compound of the formula $R^1$—CO—$CH_2$—CO—$R^2$ wherein $R^1$ and $R^2$ are independently an aliphatic, aromatic or heterocyclic moiety.

7. The process according to claim 6, wherein $R^1$ and $R^2$ are independently phenyl or substituted phenyl.

8. The process according to claim 7, wherein $R^1$ is p-tert.butylphenyl and $R^2$ is p-methoxyphenyl.

9. A $BF_3$-complex of 4-tert.butyl-4'-methoxy-dibenzoylmethane.

10. The process according to claim 2 wherein the organic solvent used in the reaction is an aromatic hydrocarbon.

11. The process according to claim 10 wherein the aromatic hydrocarbon is toluene.

12. The process according to claim 2 wherein the complex is decomposed by treatment with aqueous ammonia solution.

13. The process according claim 3 wherein the complex is decomposed by treatment with aqueous ammonia solution.

14. The process according to claim 4 wherein the complex is decomposed by treatment with aqueous ammonia solution.

15. The process according to claim 10 wherein the complex is decomposed by treatment with aqueous ammonia solution.

16. The process according to claim 11 wherein the complex is decomposed by treatment with aqueous ammonia solution.

17. The process according to claim 2 wherein the 1,3-diketone is a compound of the formula $R^1$—CO—$CH_2$—CO—$R^2$ wherein $R^1$ and $R^2$ are independently an aliphatic, aromatic or heterocyclic moiety.

18. The process according to claim 3 wherein the 1,3-diketone is a compound of the formula $R^1$—CO—$CH_2$—CO—$R^2$ wherein $R^1$ and $R^2$ are independently an aliphatic, aromatic or heterocyclic moiety.

19. The process according to claim 4 wherein the 1,3-diketone is a compound of the formula $R^1$—CO—$CH_2$—CO—$R^2$ wherein $R^1$ and $R^2$ are independently an aliphatic, aromatic or heterocyclic moiety.

20. The process according to claim 5 wherein the 1,3-diketone is a compound of the formula $R^1$—CO—$CH_2$—CO—$R^2$ wherein $R^1$ and $R^2$ are independently an aliphatic, aromatic or heterocyclic moiety.

* * * * *